US010407681B2

(12) United States Patent
Kamo et al.

(10) Patent No.: US 10,407,681 B2
(45) Date of Patent: Sep. 10, 2019

(54) **PLANT-MEDIATED SILENCING OF A FATTY ACID AND RETINOID BINDING PROTEIN IN *PRATYLENCHUS PENETRANS***

(71) Applicants: The United States of America, as represented by the Secretary of Agriculture, Washington, DC (US); VIRGINIA TECH UNIVERSITY, Blacksburg, VA (US)

(72) Inventors: Kathryn K. Kamo, Colubmia, MD (US); Paulo C. R. Vieira, Washington, DC (US); Jonathan D. Eisenback, Blacksburg, VA (US)

(73) Assignees: The United States of America, as represented by The Secretary of Agriculture, Washington, DC (US); Virginia Tech Intellectual Properties, Inc., Blacsburg, VA (US)

( * ) Notice: Subject to any disclaimer, the term of this patent is extended or adjusted under 35 U.S.C. 154(b) by 0 days.

(21) Appl. No.: 15/936,703

(22) Filed: Mar. 27, 2018

(65) Prior Publication Data

US 2018/0282727 A1 Oct. 4, 2018

Related U.S. Application Data

(60) Provisional application No. 62/477,548, filed on Mar. 28, 2017.

(51) Int. Cl.

| | |
|---|---|
| ***C07H 21/04*** | (2006.01) |
| ***C12N 15/113*** | (2010.01) |
| ***A01N 57/16*** | (2006.01) |

(52) U.S. Cl.
CPC ............ *C12N 15/113* (2013.01); *A01N 57/16* (2013.01); *C12N 2310/111* (2013.01); *C12N 2310/14* (2013.01)

(58) Field of Classification Search
CPC .................................................... C12N 15/111
See application file for complete search history.

(56) References Cited

U.S. PATENT DOCUMENTS

| | | | | |
|---|---|---|---|---|
| 8,088,976 B2 | 1/2012 | Boukharov et al. | | |
| 2013/0109740 A1 * | 5/2013 | Brown | ................ | C12N 15/113 514/44 A |

OTHER PUBLICATIONS

Tan, Jo-Anne Chiew Hwa, Characterising putative parasitism genes for root lesion nematodes and their use in RNA nterference studies. (2015), PhD thesis, Murdoch University.

* cited by examiner

*Primary Examiner* — Kimberly Chong
(74) *Attorney, Agent, or Firm* — John D. Fado; Mark. D McNemar

(57) ABSTRACT

The present disclosure provides compositions and methods utilizing double strand ribonucleic acid (dsRNA) to control parasitic nematodes, including *Pratylenchus penetrans*. More particularly, the present invention relates to several specific synthetic dsRNAs that induce RNA interference (RNAi) in the target nematodes and methods of delivering the dsRNAs to them, such as allowing feeding on plants containing the dsRNAs.

21 Claims, 5 Drawing Sheets
(2 of 5 Drawing Sheet(s) Filed in Color)
Specification includes a Sequence Listing.

SEQUENCE LISTING

<160> NUMBER OF SEQ ID NOS: 5

<210> SEQ ID NO 1
<211> LENGTH: 291
<212> TYPE: DNA
<213> ORGANISM: Artificial Sequence
<220> FEATURE:
<223> OTHER INFORMATION: Chemically Synthesized

<400> SEQUENCE: 1
aaggccgttg aacttcgtaa tctggtaaag ggaaaaattg atgcgttgaa tccagatgcc 60
aaggaatttg tgaccggggt tatcgagaag ctgaaggccc ttcgaccaaa acccggtgag 120
aagccgaacc tggaagaact ccgcaagcag gctaatgaga tcgttgaaaa atacaagggg 180
ctaaatgatg aagctaaaga atctttgaag agcaactttc ccaagatcac tggaattatc 240
caaaatgaga aattccaaaa tctagcaaag agtctgctga aacccgaagg c 291

-continued

<210> SEQ ID NO 2
<211> LENGTH: 836
<212> TYPE: DNA
<213> ORGANISM: Pratylenchus penetrans

<400> SEQUENCE: 2
cccactgttt ggcctatata aaagtagagt catgaaggct cagaccaaca tttggtctta 60
tcccgactat catactacta ctaccactca tccttattca caattcccct gccctgccaa 120
acccagctat gtacaaggtg atttgccttc tggcctttat agccatagca caagcagcag 180
taattccacc tttggatctt aattccatcc cagaagaata tcgtgatttg gttccaccgg 240
aagtcaccac tttctacaat gaactcacgg aagaagacaa acagatactg aaggagatag 300
caagccgtca tgaggaattc caaaacgagg accaggctct ggaagctttg aaaaccaaaa 360
gtgaaaaact ctacaataag gccgttgaac ttcgtaatct ggtaaaggga aaaattgatg 420
cgttgaatcc agatgccaag gaatttgtga ccggggttat cgagaagctg aaggcccttc 480
gaccaaaacc cggtgagaag ccgaacctgg aagaactccg caagcaggct aatgagatcg 540
ttgaaaaata caaggggcta aatgatgaag ctaaagaatc tttgaagagc aactttccca 600
agatcactgg aattatccaa aatgagaaat tccaaaatct agcaaagagt ctgctgaaac 660
ccgaaggcgc tgccccagct gcttaaaagg gaatgagggc attaattgaa acaaaaactt 720
taatacacgc atatatatgt cgaaatgttg gtgaaaataa agagaattgg gctgggaaag 780
gatattaacc aattcttaat aaaaaaatgc tgacaaaaaa aaaaaaaaaa aaaaaa 836

<210> SEQ ID NO 3
<211> LENGTH: 665
<212> TYPE: DNA
<213> ORGANISM: Pratylenchus penetrans

<400> SEQUENCE: 3
catttggtct tatcccgact atcatactac tactaccact catccttatt cacaattccc 60
ctgccctgcc aaacccagct atgtacaagg tgatttgcct tctggccttt atagccatag 120
cacaagcagc agtaattcca cctttggatc ttaattccat cccagaagaa tatcgtgatt 180
tggttccacc ggaagtcacc actttctaca atgaactcac ggaagaagac aaacagatac 240
tgaaggagat agcaagccgt catgaggaat tccaaaacga ggaccaggct ctggaagctt 300
tgaaaaccaa aagtgaaaaa ctctacaata aggccgttga acttcgtaat ctggtaaagg 360
gaaaaattga tgcgttgaat ccagatgcca aggaatttgt gaccggggtt atcgagaagc 420
tgaaggccct tcgaccaaaa cccggtgaga agccgaacct ggaagaactc cgcaagcagg 480
ctaatgagat cgttgaaaaa tacaaggggc taaatgatga agctaaagaa tctttgaaga 540
gcaactttcc caagatcact ggaattatcc aaaatgagaa attccaaaat ctagcaaaga 600
gtctgctgaa acccgaaggc gctgccccag ctgcttaaaa gggaatgagg gcattaattg 660
aaaca 665

<210> SEQ ID NO 4
<211> LENGTH: 807
<212> TYPE: DNA
<213> ORGANISM: Pratylenchus penetrans

<400> SEQUENCE: 4
atgtacaagg tgatttgcct tctggccttt atagccatag cacaagcagc agtaattcca 60

-continued

```
cctttggatc ttaattccat cccagaagaa tatcgtggta tgttttaagc aaggaaagat    120

tgaaggaata ataatcacat gaaatttcac agatttggtt ccaccggaag tcaccacttt    180

ctacaatgaa ctcacggaag aagacaaaca gatactgaag gagatagcaa gccgtcatga    240

ggaattccaa aacgaggacc aggctctgga agctttgaaa accaaaagtg aaaaactcta    300

caataaggta tgttatggga aattagccat aataaatgca actcataaag gccgttgaac    360

ttcgtaatct ggtaaaggga aaaattgatg cgttgaatcc agatgccaag gaatttgtga    420

ccggggtttg tgaaaaggat attgcatttt tagtcaattt ttatatgcat tcaggttatc    480

gagaagctga aggcccttcg accaaaaccc ggtgagaagc cgaacctgga agaactccgc    540

aagcaggcta atgagatcgt tgaaaagtaa taatttcagt tagatgattt taaactaaaa    600

agccaactgt ttagatacaa ggggctaaat gatgaagcta aagaatcttt gaagagcaac    660

tttcccaaga tcactggaat tatccaaagt aagttaacca ttaaacaatc aatgaatatt    720

ttcccacgct gcattctttc agatgagaaa ttccaaaatc tagcaaagag tctgctgaaa    780

cccgaaggcg ctgccccagc tgcttaa                                        807


<210> SEQ ID NO 5
<211> LENGTH: 185
<212> TYPE: PRT
<213> ORGANISM: Pratylenchus penetrans

<400> SEQUENCE: 5

Met Tyr Lys Val Ile Cys Leu Leu Ala Phe Ile Ala Ile Ala Gln Ala
1               5                   10                  15

Ala Val Ile Pro Pro Leu Asp Leu Asn Ser Ile Pro Glu Glu Tyr Arg
            20                  25                  30

Asp Leu Val Pro Pro Glu Val Thr Thr Phe Tyr Asn Glu Leu Thr Glu
        35                  40                  45

Glu Asp Lys Gln Ile Leu Lys Glu Ile Ala Ser Arg His Glu Glu Phe
    50                  55                  60

Gln Asn Glu Asp Gln Ala Leu Glu Ala Leu Lys Thr Lys Ser Glu Lys
65                  70                  75                  80

Leu Tyr Asn Lys Ala Val Glu Leu Arg Asn Leu Val Lys Gly Lys Ile
                85                  90                  95

Asp Ala Leu Asn Pro Asp Ala Lys Glu Phe Val Thr Gly Val Ile Glu
            100                 105                 110

Lys Leu Lys Ala Leu Arg Pro Lys Pro Gly Glu Lys Pro Asn Leu Glu
        115                 120                 125

Glu Leu Arg Lys Gln Ala Asn Glu Ile Val Glu Lys Tyr Lys Gly Leu
    130                 135                 140

Asn Asp Glu Ala Lys Glu Ser Leu Lys Ser Asn Phe Pro Lys Ile Thr
145                 150                 155                 160

Gly Ile Ile Gln Asn Glu Lys Phe Gln Asn Leu Ala Lys Ser Leu Leu
                165                 170                 175

Lys Pro Glu Gly Ala Ala Pro Ala Ala
            180                 185
```

PLANT-MEDIATED SILENCING OF A FATTY ACID AND RETINOID BINDING PROTEIN IN *PRATYLENCHUS PENETRANS*

CROSS-REFERENCE

This present application claims priority under 35 U.S.C. § 119(e) to U.S. Provisional Ser. No. 62/477,548, which was filed on Mar. 28, 2017, and is hereby incorporated by reference.

BACKGROUND OF THE INVENTION

Field of Invention

The present disclosure provides compositions and methods utilizing double strand ribonucleic acid (dsRNA) to control parasitic nematodes, including *Pratylenchus penetrans*. More particularly, the present invention relates to several specific synthetic dsRNAs that induce RNA interference (RNAi) in the target nematodes and methods of delivering the dsRNAs to them.

Background

Root lesion nematodes are considered the third most important group among plant-parasitic nematodes (Jones et al., Mol. Plant Pathol., (2013) 14:946-61). Within this group of nematodes, *Pratylenchus penetrans* (Cobb, 1917) Filipjev & Schuurmans Stekhoven, 1942 is considered a cosmopolitan species worldwide, having a preferential distribution along temperate regions. This species has been recorded as being associated with more than 400 plants, and considered to be a limiting factor for the production of important agronomic [e.g. alfalfa (*Medicago sativa* L.), corn (*Zea mays* subsp. mays L.), potato (*Solanum tuberosum* L.)], ornamental [e.g. lily (*Lilium candidum* L.), roses (*Rosa* spp.)] and fruit plants [e.g. apple (*Malus pumila* Miller), cherry orchards (*Prunus* spp.), raspberry (*Rubus* spp.)] (Castillo and Vovlas, in "*Pratylenchus* (Nematoda: Pratylenchidae): diagnosis, biology, pathogenicity and management. Nematology Monographs and Perspectives, 6" Brill Leiden-Boston, The Netherlands-USA (2007) p. 529). In some countries *P. penetrans* is considered as an A1 quarantine plant pest due to its potential impact on economic important crops (EPPO Global database).

Like other nematodes, the life cycle of *P. penetrans* is punctuated by six stages (eggs, four juvenile stages and adults). With the exception of the egg and J1 stages, all the remaining stages are motile and able to enter the roots and cause damage (Castillo & Vovlas, supra). This nematode is a migratory endoparasitic species that feeds and migrates within the root cortical tissue causing a reduction in root growth after infection, accompanied by the formation of lesions, necrotic areas, browning and cell death (Fosu-Nyarko & Jones, Ann. Rev. Phytopathol., (2016) 54:253-78). As migratory endoparasites the destruction of the root system can cause surface wounds, which allow access to a combination of other soil borne pathogens, such as fungi (Rotenberg et al., Plant Pathol., (2004) 53:294-302) and bacteria (Vrain et al., Can. J. Plant Pathol., (1987) 9:236-40), leading to a severe damage of the plant.

Silencing core genes through RNA interference (RNAi) can promote lethal or inhibitory effects (Lilley et al., Parasitol. (2012) 139:630-40; Danchin et al., PLoS Pathogens (2013) 9:e1003745), making it is a very promising tactic in the control of plant-parasitic nematodes. However, one imperative factor is the identification of plant-pathogen specific genes, or target sequences, that lack homologs in non-target organisms such as mammals, plants or beneficial insects (Danchin et al., supra).

Fatty-acid and retinol-binding proteins (FARs) comprise a family of unusual α-helix rich lipid-binding proteins, which have high binding affinity for fatty acids, retinol and retinoic acids, and are exclusively found within the phylum Nematoda (Kennedy et al., "The unusual lipid-binding proteins of nematodes: NPAs, nemFABPs and FARs", In Parasitic nematodes: molecular biology, biochemistry and immunology, eds. Kennedy MW, Harnett W. CABI, Wallingford, UK. (2013) pp. 397-412). This family of proteins occurs in several isoforms of approximately 20 kDA, which can be found in varying numbers among species of the different clades of Nematoda (Garofalo et al., J. Biol. Chem., (2003) 278:8065-74; Iberkleid et al., Eur. J. Plant Pathol. (2015) 143:133-49). In the case of free-living nematodes, eight isoforms have been found within the genome of *Caenorhabditis elegans* (Maupas, 1900) Dougherty, 1955 (Garofalo et al., supra), whereas in *Pristionchus pacificus* Sommer, Carta, Kim & Sternberg, 1996, nineteen members have been identified (Dieterich et al., Nature Genetics (2008) 40:1193-98; Dillman et al., Genome Biol., (2015) 16:e200). In the case of animal- and plant-parasitic nematodes the number of effective FAR isoforms is still unknown. In *Necator americanus* (Stiles, 1902) Stiles, 1906 at least six FAR genes have been identified, while for a substantial portion of studied species so far, a single gene has been reported (Kennedy et al., J. Biol. Chem., (1997) 272:29442-48; Garofalo et al., 2003, supra; Tang et al., Nature Genetics (2014) 46:261-71; Iberkleid et al., 2015, supra). In plant-parasitic nematodes, a single FAR gene has been reported for both sedentary [e.g. *Globodera pallida* (Stone, 1973) Behrens, 1975 (Prior et al., Biochem. J. (2001) 356:387-94), *Meloidogyne javanica javanica* (Treub, 1885) Chitwood, 1949 (Iberkleid et al., PLoS One, (2013) 8:e64586), *Heterodera avenae* Wollenweber, 1924 (Le et al., 2016) and H. filipjevi (Madzhidov, 1981) Stelter, 1984 (Qiao et al., 2016)] and migratory [e.g. *Aphelenchoides besseyi* Christie, 1942 (Cheng et al., PLoS One, (2013) 8:e66011), *Radopholus similis* (Cobb, 1893) Thorne, 1949 (Zhang et al., PLoS One (2015) 10:e0118414)] species. More recently, comparative transcriptome and genomic data suggested that plant-parasitic species (e.g. *Bursaphelenchus xylophilus* (Steiner & Buhrer, 1934) Nickle, 1970 and *Heterodera avenae*) have additional members of this FAR family (Dillman et al., supra; Espada et al., Mol. Plant Pathol., (2016) 17:286-95; Qiao et al., PLoS One, (2016) 11:e0160003). In entomopathogenic nematode species of the genus *Steinernema*, a wide expansion of the number of genes within the FAR family have been reported, ranging between 38 to 54 gene members of this family (Dillman et al., supra).

FAR proteins seem to play a relevant role in the binding of lipids from their environment or host, as nematodes are unable to synthesize de novo fatty acids (Kennedy et al., 2013, supra). A wide range of functions has been implicated for nematode FARs, such as scavenging, transport and metabolism of hydrophobic lipophilic molecules like fatty acids, eicosanoids, retinoids, and steroids (McDermott et al., Mol. Cell. Biochem., (1999) 192:69-75); Kennedy, Biochim. Biophys. Acta, (2000) 1476:146-64). These proteins have important functions as energy sources and are used in the metabolic and developmental processes such as embryogenesis, glycoprotein synthesis, growth and cellular differentiation (McDermott et al., supra; Kennedy, 2000, supra). In addition to their role in the nematode's physiological activity, FARs have raised strong interest because of their implication in the parasitism process of both animal- and plant-parasitic nematodes (Kennedy et al., 1997, supra; Bradley et al., Trends Parasitol., (2001) 17:471-475; Prior et al., supra; Iberkleid et al., 2013, supra).

Previously we have identified in the transcriptome of *P. penetrans* a highly abundant transcript encoding for a fatty acid- and retinoid-binding gene (Vieira et al., PLoS One, (2015) 10:e0144674). Along the in silico analyses carried out along this study we were able to identify three different FARs members of this family to *P. penetrans*. We set out to confirm the expression levels of Pp-far-1 in different nematode developmental stages, and at earlier time points of nematode infection in different host plants. Pp-far-1 was then targeted using plant-mediated RNAi silencing assays to evaluate the importance of this gene during parasitism. Based on our RNAi analyses, knocking-down this gene via RNAi is an option to control this species.

SUMMARY OF THE INVENTION

Provided herein are multiple embodiments of the disclosed invention, including a double-stranded ribonucleic acid (dsRNA) having two strands, where the sequence of the first strand has at least 95% identity to a portion of at least 19 consecutive nucleotides of SEQ ID NO:1, SEQ ID NO:2, or SEQ ID NO:3 and the second strand is complementary to the first strand. In some embodiments, the first strand of the dsRNA has at least 99% or 100% sequence identity to any one of SEQ ID NOs. 1, 2, or 3. In particular embodiments, the first strand is SEQ ID NO. 1, SEQ ID NO. 2, or SEQ ID NO. 3. In some embodiments, dsRNAs of the present invention are expressed in a plant cell. In other embodiments, dsRNAs of the present invention are distributed throughout at least part of a living plant, such as corn, soybean or lily. In preferred embodiments, a dsRNA according to the invention is capable of inducing ribonucleic acid interference (RNAi) when ingested by a nematode, for example *Pratylenchus penetrans*.

In an additional embodiment of the present invention, provided herein is a DNA molecule comprising a promoter functional in a host cell and a DNA encoding a dsRNA having two strands, where the sequence of the first strand has at least 95% identity to a portion of at least 19 consecutive nucleotides of SEQ ID NO:1, SEQ ID NO:2, or SEQ ID NO:3 and the second strand is complementary to the first strand. In some embodiments, the host cell for such DNA molecules is a plant cell. Thus, host cells comprising such DNA are yet another embodiment disclosed herein.

Further provided herein are plant cells, plants and seeds comprising any of the dsRNA species provided herein. In particular embodiments, plant cell, plant or seed contains a DNA molecule that allows for the expression of the dsRNA. In other embodiments, the dsRNA is taken up by the plant cell, plant or seed after topical application of a composition containing any dsRNA of the present invention.

Still further provided herein are methodologies for inducing RNA interference (RNAi) in a nematode, such as *Pratylenchus penetrans*, comprising the steps of allowing the nematode to feed on a plant comprising any dsRNA disclosed herein such that the dsRNA is ingested by the nematode, thereby inducing RNAi. In some embodiments, one strand of the dsRNA utilized for such methods is identical to SEQ ID NO. 1, SEQ ID NO. 2, or SEQ ID NO. 3. In particular embodiments, the plant is corn, lily or soybean.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The patent application file contains at least one drawing executed in color. Copies of this patent or patent application publication with color drawing(s) will be provided by the Office upon request and payment of the necessary fee.

The novel features of the invention are set forth with particularity in the claims. Features and advantages of the present invention are referred to in the following detailed description, and the accompanying drawings of which:

(FIG. 1A) The amplification was performed on cDNA collected from males, females, juveniles (J2, J3 and J4) and eggs, respectively. The Pp-far-1 gene expression was initially detected for the different developmental stages by a semi-quantitative RT-PCR (gel images). The transcript expression levels were then quantified by RT-qPCR, and normalized with the *P. penetrans* 18S rRNA gene. Relative expression values represent changes of the expression levels of the different nematode stages relative to the expression of Pp-far-1 in the eggs. Data shown represent the means of three independent repetitions plus standard error. Letters indicate statistically significant differences between mean values among the different nematode stages ($P<0.05$). (FIG. 1B, FIG. 1C, FIG. 1D, FIG. 1E) Whole mount in situ hybridization of Pp-far-1, and sense probe (FIG. 1E), showing the detection of the digoxigenin-labeled probe hybridized to Pp-far-1 transcripts along the hypodermis (brown color) in different sections of the nematode body using the antisense probe (FIG. 1B-D), while in the control sections no signal was detected with the sense probe (e). Scale bars=10 μm.

(FIG. 3A) For selection of transformed hairy roots, PCR detection was used for the presence of the Pp-far-1 gene fragment in the soybean hairy roots. (FIG. 3B) Semi-quantitative RT-PCR of the pRAP17 intron of the hairpin dsRNA was used to confirm the expression levels of Pp-far-1 dsRNA in soybean hairy root lines 1 to 15. Lines L4, L7, L8 and L13 were selected for nematode challenge assays due to their growth performance and intron expression levels.

(FIG. 4A) Nematode challenge assays in transgenic soybean (*Glycines* max (L.) Merr.) dsRNA hairy root lines 3 months after infection. Data shown represent the total mean number±SEM of nematodes recovered from roots, using a pool of nine soybean hairy roots for each line. Replicate 1 and replicate 2 correspond to two independent biological assays, using the same hairy root lines. As a control, hairy roots transformed with an empty vector (pBinJIT) were used. Asterisks denote statistically significant differences between values of each individual line against control ($P<0.05$). (FIG. 4B) Transcript levels of *P. penetrans* targeting genes that develop in the dsRNA expressing transgenic soybean hairy root lines. The expression levels were quantified using Pp-18S rRNA gene as reference. Each bar represents the mean with standard error of a set of nematodes collected from infected roots, using three technical repetitions. Asterisks denote statistically significant differences between values of each individual line against control ($P<0.05$).

(FIG. 5A) For selection of transformed hairy roots PCR detection was used for the presence of the NTPII fragment. (FIG. 5B) Expression of the NPTII gene was confirmed by semi-quantitative RT-PCR of the hairy root lines, and UBQ3 gene was used as a positive reference control. Lines L1, L3 and L4 were selected for nematode challenge assays.

DETAILED DESCRIPTION OF THE INVENTION

Figure 1A:
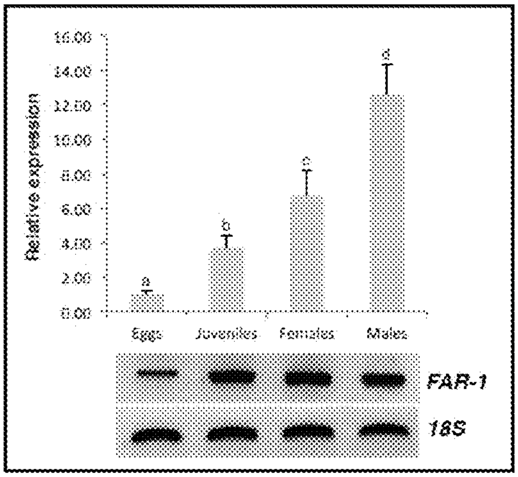
FIG. 1A-1E provide results from experiments determining Pp-far-1 expression levels during different nematode developmental stages, and in situ tissue localization of Pp-far-1 in *Pratylenchus penetrans* (Cobb, 1917) Filipjev & Schuurmans Stekhoven, 1942.

Preferred embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby.

Technical and scientific terms used herein have the meanings commonly understood by one of ordinary skill in the art to which the instant invention pertains, unless otherwise defined. Reference is made herein to various materials and methodologies known to those of skill in the art. Standard reference works setting forth the general principles of recombinant DNA technology include Sambrook et al., "Molecular Cloning: A Laboratory Manual", 2d ed., Cold Spring Harbor Laboratory Press, Plainview, N.Y., 1989; Kaufman et al., eds., "Handbook of Molecular and Cellular Methods in Biology and Medicine", CRC Press, Boca Raton, 1995; and McPherson, ed., "Directed Mutagenesis: A Practical Approach", IRL Press, Oxford, 1991.

Any suitable materials and/or methods known to those of skill can be utilized in carrying out the instant invention. Materials and/or methods for practicing the instant invention are described. Materials, reagents and the like to which reference is made in the following description and examples are obtainable from commercial sources, unless otherwise noted.

RNA interference (RNAi) is a double stranded RNA (dsRNA) or small interfering RNA (siRNA) mediated gene-silencing mechanism that exists in animals and plants. RNAi has become a useful technology for functional gene regulation and provides a potential tool for development of bio-molecular pesticides. Described herein, molecular biopesticides detrimental to *Pratylenchus penetrans*, a plant-parasitic nematode, were generated from in vitro transcribed double stranded RNAs (dsRNAs) designed to target specific gene sequences. Although in vitro expression of a dsRNA by a transgenic plant is one mechanism to deliver the sequences of the present invention to target nematodes, any mechanism known in the art can be utilized, but preferably one that allows for ingestion.

Provided herein are methods and compositions for providing dsRNAs capable of controlling nematode pests, preferably by feeding. In some embodiments, dsRNA species are delivered to the animals via feeding on transgenic plants expressing the dsRNAs. In other embodiments, the dsRNAs are delivered to the animals via feeding on plants that have taken up exogenous dsRNAs, or via feeding on alternate sources of the dsRNAs.

Definitions

As used in the specification and claims, use of the singular "a", "an", and "the" include plural references unless the context clearly dictates otherwise.

The terms isolated, purified, or biologically pure as used herein, refer to material that is substantially or essentially free from components that normally accompany the referenced material in its native state.

The term "about", "approximately", and similar terms are defined as plus or minus ten percent of a recited value. For example, about 1.0 g means from a range of 0.9 g to 1.1 g and all values within that range, whether specifically stated or not.

The term "gene" refers to a DNA sequence involved in producing a RNA or polypeptide or precursor thereof. The polypeptide or RNA can be encoded by a full-length coding sequence or by intron-interrupted portions of the coding sequence, such as exon sequences.

The term "oligonucleotide" refers to a molecule comprising a plurality of deoxyribonucleotides or ribonucleotides. Oligonucleotides may be generated in any manner known in the art, including chemical synthesis, DNA replication, reverse transcription, polymerase chain reaction, or a combination thereof. In one embodiment, the present invention embodies utilizing the oligonucleotide in the form of dsRNA as means of interfering with a critical developmental or reproductive process that leads to control. Inasmuch as mononucleotides are synthesized to construct oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

The term "a nucleic acid consisting essentially of", and grammatical variations thereof, means nucleic acids that differ from a reference nucleic acid sequence by 20 or fewer nucleic acid residues and also perform the function of the reference nucleic acid sequence. Such variants include sequences that are shorter or longer than the reference nucleic acid sequence, have different residues at particular positions, or a combination thereof.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide, which is capable of acting as a point of initiation of synthesis when placed under conditions in which primer extension is initiated. An oligonucleotide "primer" may occur naturally, as in a purified restriction digest or may be produced synthetically.

A primer is selected to be "substantially complementary" to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence is sufficiently complementary with the sequence of the template to hybridize and thereby form a template primer complex for synthesis of the extension product of the primer.

As used herein, "dsRNA" refers to double-stranded RNA that comprises a sense and an antisense portion of a selected target gene (or sequences with high sequence identity thereto so that gene silencing can occur), as well as any smaller double-stranded RNAs formed therefrom by RNAse or dicer activity. Such dsRNA can include portions of single-stranded RNA, but contains at least 19 nucleotides double-stranded RNA. In one embodiment of the invention, a dsRNA comprises a hairpin RNA which contains a loop or spacer sequence between the sense and antisense sequences of the gene targeted, preferably such hairpin RNA spacer region contains an intron, particularly the rolA gene intron (Pandolfini et al., 2003, BioMedCentral (BMC) Biotechnology 3:7 (www.biomedcentral.com/1472-6750/3/7)), the dual orientation introns from pHellsgate 11 or 12 (see, WO 02/059294 and SEQ ID NO: 25 and 15 therein) or the pdk intron (*Flaveria trinervia* pyruvate orthophosphate dikinase intron 2; see WO99/53050).

Included in this definition are "siRNAs" or small interfering (double-stranded) RNA molecules of 16-30 bp, 19-28 bp, or 21-26 bp, e.g., such as the RNA forms that can be created by RNAseIII or dicer activity from longer dsRNA. siRNAs as used herein include any double-stranded RNA of 19 to 26, or 21 to 24 base pairs that can interfere with gene expression when present in a cell wherein such gene is expressed. siRNA can be synthetically made, expressed and secreted directly from a transformed cell or can be generated from a longer dsRNA by enzymatic activity. These siRNAs can be blunt-ended or can have overlapping ends. Also, modified microRNAs comprising a portion of a target gene and its complementary sequence are included herein as dsRNAs.

Sequences or parts of sequences which have "high sequence identity", as used herein, refers to the number of positions with identical nucleotides divided by the number of nucleotides in the shorter of the sequences, being higher than 95%, higher than 96%, higher than 97%, higher than 98%, higher than 99%, or between 96% and 100%. A target gene, or at least a part thereof, as used herein, preferably has high sequence identity to the dsRNA of the invention in order for efficient gene silencing to take place in the target pest. Identity in sequence of the dsRNA or siRNA with a part of the target gene RNA is included in the current invention but is not necessary.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other is regarded as a position with non-identical residues. The alignment of the two sequences is performed by the Needleman and Wunsch algorithm (Needleman and Wunsch, J Mol Biol, (1970) 48:3, 443-53). A computer-assisted sequence alignment can be conveniently performed using a standard software program such as GAP which is part of the Wisconsin Package Version 10.1 (Genetics Computer Group, Madison, Wis., USA) using the default scoring matrix with a gap creation penalty of 50 and a gap extension penalty of 3.

For the purpose of the invention, the "complement of a nucleotide sequence X" is the nucleotide sequence which would be capable of forming a double-stranded DNA or RNA molecule with the represented nucleotide sequence, and which can be derived from the represented nucleotide sequence by replacing the nucleotides by their complementary nucleotide according to Chargaff's rules (A< >T; G< >C; A< >U) and reading in the 5' to 3' direction, i.e., in opposite direction of the represented nucleotide sequence.

A dsRNA "targeting" a gene, mRNA or protein, as used herein, refers to a dsRNA that is designed to be identical to, or have high sequence identity to, one or more mRNAs endogenous to the target organism (the target genes), and as such is designed to silence such gene upon application to such organisms (e.g., nematodes). One dsRNA can target one or several homologous target genes in one nematode or one or several homologous target genes in different nematodes which can feed on the same host plant. One of skill in the art will recognize that multiple currently-known genes, as well as other currently unknown or uncharacterized genes can be targeted by applying the teachings herein.

"Nematodicidal activity" of a dsRNA, as used herein, refers to the capacity to obtain mortality in nematodes when such dsRNA is fed to nematodes, which mortality is significantly higher than a negative control (using a non-nematode dsRNA or buffer).

"Nematode control" using a dsRNA, as used herein, refers to the capacity to inhibit nematode development, fertility, inhibition of pheromone production, or growth in such a manner that the nematode population provides less damage to a plant, produces fewer offspring, are less fit or are more susceptible to predator attack, or that nematodes are even deterred from feeding on such plant.

The term "corresponds to" as used herein means a polynucleotide sequence homologous to all or a portion of a reference polynucleotide sequence, or a polypeptide sequence that is identical to a reference polypeptide sequence. In contradistinction, the term "complementary to" is used herein to mean that the complementary sequence is homologous to all or a portion of a reference polynucleotide sequence. For example, the nucleotide sequence "TATAC" corresponds to a reference sequence "TATAC" and is complementary to a reference sequence "GTATA". An "RNA from" of a DNA sequence, as used herein is the RNA sequence of said DNA, so the same sequence but wherein the T nucleotide is replaced by a U nucleotide.

The term "plant" includes whole plants, plant organs, progeny of whole plants or plant organs, embryos, somatic embryos, embryo-like structures, protocorms, protocorm-like bodies (PLBs), and suspensions of plant cells. Plant organs comprise, e.g., shoot vegetative organs/structures (e.g., leaves, stems and tubers), roots, flowers and floral organs/structures (e.g., bracts, sepals, petals, stamens, carpels, anthers and ovules), seeds (including embryo, endosperm, and seed coat) and fruit (the mature ovary), plant tissue (e.g., vascular tissue, ground tissue, and the like) and cells (e.g., guard cells, egg cells, trichomes and the like). Any plant on which *P. penetrans* nematodes feed are included in this invention.

An "effective amount" is an amount sufficient to effect desired beneficial or deleterious results. An effective amount can be administered in one or more administrations. In terms of treatment, an "effective amount" is that amount sufficient to make the target pest non-functional by causing an adverse effect on that pest, including (but not limited to) physiological damage to the pest; inhibition or modulation of pest growth; inhibition or modulation of pest reproduction; or death of the pest. In one embodiment of the invention, a dsRNA containing solution is fed to a target nematode wherein critical developmental and/or reproductive functions of said nematode are disrupted as a result of ingestion.

General Overview

Double-stranded RNA (dsRNA) mediated gene silencing, also known as RNA interference (RNAi), is a breakthrough technology for functional genomic studies providing a potential tool for management of agricultural and horticultural nematode pests. Since the inception of RNAi numerous studies have documented successful introduction of synthetic dsRNA or siRNA into the organism that triggers a highly efficient gene silencing through degradation of endogenous RNA homologous to the presented dsRNA/siRNA. One focus of the present invention is providing for RNAi-mediated control of parasitic nematodes, namely *P. penetrans*.

*P. penetrans* is one of the most important plant-parasitic nematodes that can decimate important agricultural, horticultural and industrial crops. Fatty acid- and retinoid-binding proteins are unique to nematodes, thus, such proteins, if capable of being targeted with RNAi techniques could make for a biopesticide target. The cDNA corresponding to a putative *P. penetrans* fatty acid- and retinol-binding protein was cloned and characterized molecularly for the first time for this genus as reported herein.

RNAi technology can serve as a viable tool for control and management of this voracious pest, however, the major obstacle to utilizing RNAi approaches is the challenge of delivery of effective amounts of dsRNA to the target nematodes. Mechanical microinjection of dsRNAs and soaking dsRNA(s)-containing liquids are both methods that have been successfully utilized for eliciting effective RNAi response in laboratory studies of some species. These techniques, however, are impracticable in an agricultural setting. One approach that can be used to induce RNAi via feeding by the nematode(s) on plants containing dsRNA(s) that control the nematode by, for example, increasing mortality, decreasing fertility, or otherwise decreasing the damage done to target plants. One method to introduce dsRNA(s) into plants is to construct transgenic plants expressing dsRNA species targeting nematodes such as *P. penetrans* that are important to that particular plant (see, e.g., PCT Appl. No. WO2001037654). Alternately, dsRNAs can be applied physically to a target plant, allowing for uptake of the dsRNA and distribution throughout the plant (Hunter et al., Soc. Southwestern Entomologists (2012) 37(1):85-87).

To be relevant for agricultural or horticultural control, delivery of dsRNA to target pests should be economical, efficient and advantageous. dsRNA delivered through ingestion of its solution directly (Baum et al., supra), by feeding bacteria expressing dsRNA (Timmons and Fire, Nature, (1998) 395:854), or via a dsRNA-containing diet are other possible strategies for inducing RNAi as an agricultural pest control methodology. The compositions and methodologies disclosed herein can utilize any of these routes, as well as any other route known in the art.

Double-stranded RNA and RNA Interference

Since its inception, RNAi has proved to be a potent tool to study gene function and regulation. With the advent of bioinformatics coupled with next-generation high throughput sequencing has unveiled an array of transcriptomic data available for a wide range of species at different stages of development and tissues. To attain an effective RNAi response in the biocontrol of pests, an accurate and precise mode of dsRNA delivery, efficient uptake and dsRNA stability are of utmost consideration.

Preferably, the dsRNAs to be used in this invention target at least one nematode gene portion of at least 19 consecutive nucleotides occurring in identical sequence or with high sequence identity in the one or more target nematodes. In preferred embodiments of this invention, such dsRNAs do not silence genes of a plant host, or of other non-target animals, such as beneficial insects (e.g., pollinators), pest predators or animals such as reptiles, amphibians, birds, or mammals. Levels of identity between sequences of interest can be analyzed in available databases, e.g., by a BLAST search (see also www.ncbi.nlm.nih.gov/BLAST) or by hybridization with existing DNA libraries of representative non-target organisms.

As used herein, nucleotide sequences of RNA molecules can be identified by reference to DNA nucleotide sequences of the sequence listing. However, the person skilled in the art will understand whether RNA or DNA is meant depending on the context. Furthermore, the nucleotide sequence is identical between the types of polynucleotides except that the T-base is replaced by uracil (U) in RNA molecules.

In some embodiments, the length of the first (e.g., sense) and second (e.g., antisense) nucleotide sequences of the dsRNA molecules of the invention can vary from about 10 nucleotides (nt) up to a length equaling the length in nucleotides of the transcript of the target gene. The first and second sequences can be referred to as first and second strands. Additionally, it is understood that either the first or second sequence can be the sense or antisense strand. The length of the first or second nucleotide sequence of the dsRNA of the invention can be at least 15 nt, or at least about 20 nt, or at least about 50 nt, or at least about 100 nt, or at least about 150 nt, or at least about 200 nt, or at least about 400 nt, or at least about 500 nt. If not all nucleotides in a target gene sequence are known, it is preferred to use such portion for which the sequence is known and which meets other beneficial requirements of the invention.

It will be appreciated that the longer the total length of the first (sense) nucleotide sequence in the dsRNA of the invention is, the less stringent the requirements for sequence identity between the total sense nucleotide sequence and the corresponding sequence in the target gene becomes. The total first nucleotide sequence can have a sequence identity of at least about 75% with the corresponding target sequence, but higher sequence identity can also be used such as at least about 80%, at least about 85%, at least about 90%, at least about 95%, about 100%. The first nucleotide sequence can also be identical to the corresponding part of the target gene. However, it is preferred that the first nucleotide sequence includes a sequence of 19 or 20, or about 19 or about 20 consecutive nucleotides, or even of about 50 consecutive nucleotides, or about consecutive 100 nucleotides, or about 150 consecutive nucleotides with only one mismatch, preferably with 100% sequence identity, to the corresponding part of the target gene. For calculating the sequence identity and designing the corresponding first nucleotide sequence, the number of gaps should be minimized, particularly for the shorter sense sequences.

The length of the second (antisense) nucleotide sequence in the dsRNA of the invention is largely determined by the length of the first (sense) nucleotide sequence, and may correspond to the length of the latter sequence. However, it is possible to use an antisense sequence which differs in length by about 10% without any difficulties. Similarly, the nucleotide sequence of the antisense region is largely determined by the nucleotide sequence of the sense region, and may be identical to the complement of the nucleotide sequence of the sense region. Particularly with longer antisense regions, it is however possible to use antisense sequences with lower sequence identity to the complement of the sense nucleotide sequence, such as at least about 75% sequence identity, or least about 80%, or at least about 85%, more particularly with at least about 90% sequence identity, or at least about 95% sequence to the complement of the sense nucleotide sequence. Nevertheless, it is preferred that the antisense nucleotide sequence includes a sequence of 19 or 20, about 19 or about 20 consecutive nucleotides, although longer stretches of consecutive nucleotides such as about 50 nucleotide, or about 100 nucleotides, or about 150 nucleotides with no more than one mismatch, preferably with 100% sequence identity, to the complement of a corresponding part of the sense nucleotide sequence can also be used. Again, the number of gaps should be minimized, particularly for the shorter (19 to 50 nucleotides) antisense sequences.

In one embodiment of the invention, a dsRNA molecule may further comprise one or more regions having at least 94%, at least 95%, at least 96%, at least 97%, at least 98%, or at least 99%, sequence identity to regions of at least 19 consecutive nucleotides from the sense nucleotide sequence of the target gene, different from the at least 19 consecutive nucleotides as defined in the first region, and one or more regions having at least 94%, at least 95%, at least 96%, at least 97%, at least 98%, or at least 99%, sequence identity to at least 19 consecutive nucleotides from the complement of the sense nucleotide sequence of the target gene, different from the at least 19 consecutive nucleotides as defined in the second region, wherein these additional regions can base-pair amongst themselves.

Transgenic Plants and Plant Cells

One embodiment of the present invention provides a plant or cell comprising one or more inhibitory dsRNAs specific for one or more mRNAs of one or more *P. penetrans* genes. Inhibitory RNAs specific for one or more mRNAs means that the inhibitory RNA down-regulates the expression, or translation, of a specific mRNA. The inhibitory RNA can be single- or double-stranded or a combination thereof. For example, the present disclosure provides transgenic plants that express one or more inhibitory RNAs that down regulate expression, or translation, of one or more target genes when the one or more inhibitory RNAs are absorbed or ingested by a target nematode (e.g., *P. penetrans*).

Another embodiment provides a transgenic plant that comprises inhibitory RNA that down regulates 3, 4, 5, 6, 7, 8, 9, 10, 11, 12, 13, 14, 15, 16, 17, 18, 19, 20, or more *P. penetrans* genes. Thus, the present disclosure provides transgenic plants and transgenic plant material that are resistant to disease caused by *P. penetrans.*

Another embodiment provides a transgenic plant or transgenic cell containing or expressing one or more inhibitory nucleic acids specific for at least a portion of a nucleic acid encoding one or more *P. penetrans* genes. The inhibitory nucleic acid is typically a small inhibitory RNA or microRNA that is specific for mRNA encoding a *P. penetrans* gene involved in growth, general health, fecundity, or reproduction. In some instances, the function of the target gene (or the protein encoded by the gene) is not known.

It will be appreciated by one of skill in the art that an inhibitory nucleic acid can be RNA, DNA, or a combination thereof. Additionally, the inhibitory nucleic acid can be single or multi-stranded and can be anti-sense or enzymatic. In one embodiment, an inhibitory nucleic acid interferes with, inhibits, or reduces the translation of a target mRNA. For example, an inhibitory nucleic acid can bind to a target mRNA and induce or promote the degradation of the target mRNA or physically prevent the cellular translational machinery from translating the target mRNA into a functional protein.

In some embodiments, a dsRNA encoding sequence, encoding a dsRNA targeting any of the genes (or portions of genes) disclosed herein, can be stably or transiently inserted in a conventional manner into the genome of a single plant cell, and the so-transformed plant cell can be used in a conventional manner to produce a transformed (i.e., transgenic) plant that has increased nematode resistance. In this regard, a disarmed Ti-plasmid, containing the dsRNA chimeric gene, in *Agrobacterium tumefaciens* can be used to transform the plant cell, and thereafter, a transformed plant can be regenerated from the transformed plant cell using the procedures described in the art, for example, in EP 0116718, EP 0270822, PCT publication WO 84/02913 and published European Patent application ("EP") 0242246. Preferred Ti-plasmid vectors each contain the dsRNA chimeric gene between the border sequences, or at least located to the left of the right border sequence, of the T-DNA of the Ti-plasmid. Of course, other types of vectors can be used to transform the plant cell, using procedures such as direct gene transfer (as described, for example in EP 0233247), pollen mediated transformation (as described, for example in EP 0270356, PCT publication WO 85/01856, and U.S. Pat. No. 4,684,611), plant RNA virus-mediated transformation (as described, for example in EP 0 067 553 and U.S. Pat. No. 4,407,956), liposome-mediated transformation (as described, for example in U.S. Pat. No. 4,536,475), and other methods such as the methods for transforming certain lines of corn (e.g., U.S. Pat. No. 6,140,553; Fromm et al., Bio/Technology (1990) 8, 833-839); Gordon-Kamm et al., The Plant Cell, (1990) 2, 603-618) and rice (Shimamoto et al., Nature, (1989) 338, 274-276; Datta et al., Bio/Technology, (1990) 8, 736-740) and the method for transforming monocots generally (PCT publication WO 92/09696). For cotton transformation, the method described in PCT patent publication WO 00/71733 can be used. For soybean transformation, reference is made to methods known in the art, e.g., Hinchee et al. (Bio/Technology, (1988) 6, 915) and Christou et al. (Trends Biotech, (1990) 8, 145) or the method of WO 00/42207.

The resulting transgenic plant can be used in a conventional plant breeding scheme to produce more transgenic plants with the same characteristics, or to introduce the dsRNA chimeric gene in other varieties of the same or related plant species. Seeds, which are obtained from the transformed plants, contain the dsRNA encoding sequence as a stable genomic insert. Plants comprising a dsRNA in accordance with the invention include plants comprising, or derived from, root stocks of plants comprising the dsRNA encoding sequence of the invention, e.g., crop species or ornamental plants. Hence, any non-transgenic grafted plant parts inserted on a transformed plant or plant part are included in the invention since the RNA interference signal is transported to these grafted parts and any nematodes feeding on such grafted plant are similarly affected by the dsRNA or siRNA of the invention.

A DNA encoding a dsRNA is typically inserted in a plant cell genome so that this DNA is downstream (i.e., 3') of, and operably linked to, a plant-expressible promoter which can direct expression in plant cells. This is preferably accomplished by inserting a dsRNA encoding sequence into the plant cell genome, particularly in the nuclear or plastid (e.g., chloroplast) genome. Also, in a dsRNA encoding sequence of the invention a nuclear localization signal can be added as described in published US patent application 20030180945.

A 'plant-expressible promoter' as used herein refers to a promoter that ensures expression of a dsRNA of the invention in a plant cell. Examples of promoters directing constitutive expression in plants are known in the art and include: the strong constitutive 35S promoters (the "35S promoters") of the cauliflower mosaic virus (CaMV), e.g., of isolates CM 1841 (Gardner et al., Nucleic Acids Res, (1981) 9, 2871-2887), CabbB-S (Franck et al., Cell (1980) 21, 285-294) and CabbB-JI (Hull and Howell, Virology, (1987) 86, 482-493); promoters from the ubiquitin family (e.g., the maize ubiquitin promoter of Christensen et al., Plant Mol Biol, (1992) 18, 675-689), the gos2 promoter (de Pater et al., The Plant J (1992) 2, 834-844), the emu promoter (Last et al., Theor Appl Genet, (1990) 81, 581-588), actin promoters such as the promoter described by An et al. (The Plant J, (1996) 10, 107), the rice actin promoter described by Zhang et al. (The Plant Cell, (1991) 3, 1155-1165); promoters of the Cassava vein mosaic virus (WO 97/48819, Verdaguer et al. (Plant Mol Biol, (1998) 37, 1055-1067), the pPLEX series of promoters from Subterranean Clover Stunt Virus (WO 96/06932, particularly the S4 or S7 promoter), an alcohol dehydrogenase promoter, e.g., pAdh1S (GenBank accession numbers X04049, X00581), and the TR1' promoter and the TR2' promoter (the "TR1' promoter" and "TR2' promoter", respectively) which drive the expression of the 1' and 2' genes, respectively, of the T-DNA (Velten et al., EMBO J, (1984) 3, 2723-2730).

Alternatively, a plant-expressible promoter can be a tissue-specific promoter, i.e., a promoter directing a higher level of expression in some cells or tissues of the plant, e.g., in green tissues (such as the promoter of the PEP carboxylase). The plant PEP carboxylase promoter (Pathirana et al., Plant J, (1997) 12:293-304) has been described to be a strong promoter for expression in vascular tissue and is useful in one embodiment of the current invention. Alternatively, a plant-expressible promoter can also be a wound-inducible promoter, such as the promoter of the pea cell wall invertase gene (Zhang et al., Plant Physiol, (1996) 112:1111-1117). A 'wound-inducible' promoter as used herein means that upon wounding of the plant, either mechanically or by pest (e.g., nematode) feeding, expression of the coding sequence under control of the promoter is significantly increased in such plant. These plant-expressible promoters can be combined with enhancer elements, they can be combined with minimal promoter elements, or can comprise repeated elements to ensure the expression profile desired.

Elements which can be used to increase expression in plant cells can be: an intron at the 5' end or 3' end of the chimeric gene, or in the coding sequence of the chimeric dsRNA encoding sequence (such as between the region encoding the sense and antisense portion of the dsRNA), e.g., the hsp70 intron, besides promoter enhancer elements, duplicated or triplicated promoter regions, 5' leader sequences different from another transgene or different from an endogenous (plant host) gene leader sequence, 3' trailer sequences different from another transgene used in the same plant or different from an endogenous (plant host) trailer sequence.

A dsRNA encoding sequence of the present invention can be inserted in a plant genome so that the inserted gene part is upstream (i.e., 5') of suitable 3' end transcription regulation signals (i.e., transcript formation and polyadenylation signals). This is preferably accomplished by inserting the dsRNA chimeric gene in the plant cell genome. Preferred polyadenylation and transcript formation signals include those of the nopaline synthase gene (Depicker et al., J. Molec Appl Gen, (1982) 1, 561-573), the octopine synthase gene (Gielen et al., EMBO J, (1984) 3:835-845), the SCSV or the Malic enzyme terminators (Schunmann et al., Plant Funct Biol, (2003) 30:453-460), and the T-DNA gene 7 (Velten and Schell, Nucleic Acids Res, (1985) 13, 6981-6998), which act as 3'-untranslated DNA sequences in transformed plant cells.

In some instances, a dsRNA encoding sequence of the present invention can optionally be inserted in a plant genome as a hybrid gene, containing several dsRNA regions which target different genes. For example, a dsRNA chimeric gene can have dsRNA regions targeting 2, 3, 4, 5, 6, 7, 8, 9, 10, 11, 12, 13, 14, 15, 16, 17, 18, 19, 20 or more genes from *P. penetrans*, an additional pest species, or a combination thereof. In some embodiments, a dsRNA chimeric gene of the present invention can contain several dsRNA regions which target different portions of the same gene, or target different alleles of the same gene. Also, it is convenient to include in the transforming DNA of the invention also a selectable or scorable marker gene, such as the bar, epsps or the neo gene, so that transformed plants can easily be selected by application of glufosinate, glyphosate or kanamycin, respectively, as is well known in the art. Advantageously, the plants or seeds of the invention also comprise a glufosinate or glyphosate tolerance gene besides the dsRNA chimeric gene of the invention, so that plants can be selected using application of the relevant herbicide (glufosinate or glyphosate).

Although plant delivery of a dsRNA is an embodiment of this invention, in accordance with this invention, application of the dsRNA(s) of the invention can be done in several ways, and need not be by way of a plant expressing a dsRNA. Any method of delivery of dsRNA not contained in a plant cell is included herein, e.g., in vitro or in vivo produced dsRNA applied to an artificial diet or feed, or microbially- or yeast-expressed dsRNA. dsRNA(s) can be applied on plants on which a nematode such as *P. penetrans* feeds by spraying a solution of microbial/yeast spores/cells comprising the dsRNA of the invention, or by spraying a solution of dsRNA onto target plants. dsRNA species of the present invention can be applied on plants by spraying a culture, culture extract, culture supernatant, or a combination thereof, where the sprayed material comprises a microbe-expressed dsRNA. Thus, the present invention includes microbes comprising genetic elements allowing for the expression of any of the dsRNA species described herein.

In particular embodiments, the present invention provides a composition having an inhibitory nucleic acid specific for an mRNA or fragment thereof represented by one or more of SEQ ID NOs. 1, 2 and 3, or a fragment or homologue thereof. Typically, dsRNAs of the present invention are provided to a target nematode pest in an amount sufficient to inhibit production of the polypeptide encoded by one or more of the full-length genes targeted by SEQ ID NOs. 1, 2, and 3 or homologues and alleles thereof. For example when *P. penetrans*, or another target nematode, is feeding on a plant or cell expressing, or containing, or coated with an inhibitory nucleic acid, the nematode ingests a sufficient level of dsRNA comprising 19 or more consecutive nucleotides of SEQ ID NOs. 1, 2, or 3 to result in a phenotypic effect.

In embodiments where a dsRNA is applied to a plant, a biopesticide composition of the present invention can contain one or more phagostimulants, pesticides, fungicides, or combinations thereof. The composition can be formulated to be coated on a plant, plant part, or seed. In certain aspects the inhibitory nucleic acid is combined with one or more excipients, buffering agents, carriers, etc. excipients, buffering agents, and carriers are well known in the art. The coating can be formulated as a spray or dip so that the inhibitory nucleic acids remain on the plant material and remain able to inhibit target protein expression in *P. penetrans* as the plant matures and develops. For example, the seed of a plant can be coated with a composition comprising an amount of one or more of the disclosed inhibitory nucleic acids effective to inhibit or reduce nematode disease in the plant in combination with an excipient.

Compositions of the invention disclosed herein can be applied to soil, fruits, vegetables, crops, and any other desired target using any delivery methodology known to those of skill in the art. For example, the compositions can be applied to the desired locale via methods and forms including, but not limited to, root soaking, shank injection, sprays, granules, flood/furrow methods, sprinklers, fumigation, root soaking and drip irrigation. In embodiments of the invention where the compositions are sprayed onto a desired locale, the compositions can be delivered as a liquid, liquid suspension, emulsion, microemulsion or powder. In other embodiments, granules or microcapsules containing dsRNA(s) can be used to deliver the compositions of the invention to the plants.

The compositions of the present invention can be applied to plants and/or crops by any convenient method, for example, by using a fixed application system such as a center pivot irrigation system. Preferably, application to fields of plants and/or crops is made by air spraying, i.e., from an airplane or helicopter, or by land spraying. For example, land spraying can be carried out by using a high flotation applicator equipped with a boom, by a back-pack sprayer or by nurse trucks or tanks. One of skill in the art will recognize that these application methodologies are provided for example and that any applicable methods known in the art or developed in the future can be utilized.

Having described the invention in general, below are examples illustrating the generation and efficacy of the invention. Neither the examples, nor the general description above should be construed as limiting the scope of the invention.

EXAMPLES

Example 1

Cloning and Characterization of Pp-FAR-1

Cloning and Sequencing:

Total RNA was extracted from mixed life stages (eggs, juveniles, females and males) of *P. penetrans* using the RNEASY PLANT MINI KIT (Qiagen, Valencia, Calif., USA) following the manufacturer's instruction. RNA was then treated with RNAase-Free DNase (Qiagen, Valencia, Calif., USA) before reverse transcription. The quantity and quality of the extracted RNA was assessed by a ND-1000 Nanodrop spectrophotometer (NanoDrop). The first strand cDNA was synthetized using the iScript first-strand synthesis kit (Bio-Rad, Hercules, Calif., USA) following the manufacturer's instruction. The full length coding sequence was amplified using primers designed based on the predicted mRNA sequence obtained from the de novo assembly performed for this species (Vieira et al., supra). A CACC sequence was added to the 5' end of the forward primer to allow insertion of the amplified sequence into the pENTR™ Directional TOPO Cloning Kit (Invitrogen, Carlsbad, Calif.). The amplified Pp-far-1 cDNA fragment was gel purified and subsequently ligated into the pENTR vector (Invitrogen, Carlsbad, Calif.), and used to transform One Shot TOP10 (Invitrogen, Carlsbad, Calif.) chemically competent *Escherichia coli* cells, which were spread on L-agar plates with kanamycin, and growth overnight at 37° C. Three insert-positive clones were used to inoculate 3 ml LB, grown overnight at 37° C., followed by plasmid DNA extraction (QIAprep Spin Miniprep Kit, QIAGEN, Inc.), and sequenced by Macrogen USA (Maryland, USA).

Sequence Analysis:

The nucleotide and translated amino acid sequences were analyzed for similarity to other genes and proteins using BLAST analyses against the NCBI non-redundant nucleotide and protein databases (www.ncbi.nlm.nih.gov). In addition, protein sequence analyses were conducted through the following programs: SignalP 4.0 was used to predict protein signal peptide (Petersen et al., Nature Meth. (2011) 8:785-6), the protein molecular mass using and theoretical isoelectric point ProtParam (Wilkins et al., Meth. Mol. Biol. (1999) 112:531-552), and secondary structure prediction of the protein sequence was performed using CLC Main Workbench v. 7 software.

The obtained coding sequence and predicted Pp-FAR-1 protein were used to perform Blast searches to different transcriptome datasets of *P. penetrans* (Vieira et al., supra) in order to detect additional members of this family. Protein sequences obtained were then aligned with other representative nematode FAR proteins using MUSCLE (Edgar, R. C., Nucl. Acids Res. (2004) 32:1792-7). Aligned protein sequences were then evaluated by distance analysis using CLC software's neighbor-joining package. To evaluate the branch strength of the phylogenetic tree, a bootstrap analysis was evaluated with 1000 replications.

Results:

Previously, a transcript encoding for a fatty acid- and retinoid-binding gene highly abundant in the transcriptome dataset of *P. penetrans* (Vieira et al., supra). In silico analyses revealed a predicted mRNA sequence of 836 nucleotides with a 558 bp open reading frame (ORF), a 5'UTR region of 117 nucleotides before the ATG initiation codon and a 3' terminal region of 128 nucleotides composed by the 3'UTR and the polyA tail sequence (SEQ ID NO:2). Based on this sequence, specific primers flanking the full-length coding sequence and partial sequences of both UTR regions were designed, resulting in the amplification of a PCR product of 665 bp, with a corresponding coding sequence of 558 bp (SEQ ID NO:3). Sequencing results revealed a nucleotide sequence showing 100% similarity to the generated de novo assembly, with highest similarity towards the *Radopholus similis* far-1 gene (77%, accession number: JN968974).

Translation of the Pp-far-1 ORF revealed 185 amino acids with a predicted molecular size of 20.82 kDa and a pI of 5.49. A signal peptide for secretion predicted by SignalP 4.0 locates between the amino acids Ala16 and Ala17 (SEQ ID NO:5), and no predicted transmembrane domains (TM-HMM server), suggesting that this protein is secreted by the nematode. As in other nematode FAR proteins, the secondary structure of Pp-FAR-1 presents a mostly alpha-helical conformation.

Protein Blast searches of Pp-FAR-1 (minimum E-value cutoff<1e$^{-5}$) in different public databases showed different ranges of similarities among other nematode FAR proteins. The alignment of the deduced Pp-FAR-1 protein with FARs of other plant-parasitic nematodes showed variable sequence conservation, with highest similarity ranging from 90% to 80% for FAR-1 of *Pratylenchus vulnus* Allen and Jensen, 1951 (Accession No. PVP01247_1 (Nematode.net)) and *Radopholus similis* (Accession No. AFI80890.1 (NCBI)) Family Pratylenchidae), 75% to 70% for *Heterodera avenae* (Accession No. ALX34942.1 (NCBI)) and *Globodera pallida* (Accession No. CAA70477.2 (NCBI)) (Family Heteroderidae), 68% for FAR-1 of *Meloidogyne javanica* (Accession No. AFZ7709.1 (NCBI)) (Family Meloidogynidae), and 55% to 51% for *Aphelenchoides besseyi* (Accession No. AGA60308.1 (NCBI)) and *Bursaphelenchus xylophilus* (Accession No. BUX.s00422.202 (GeneDB)) (Family Aphelenchoididae), while similarity to animal-parasitic nematodes ranged from 54% to 51% between *Onchocerca volvulus* Bickel, 1982 (Accession No. Q25619.1 (NCBI)) and *Brugia malayi* Brug, 1927 (Accession No. CDP95790.1 (NCBI)) (Family Onchocerdidae), and 41% to FAR-1 of the free-living nematode *Caenorhabditis elegans* (Accession No. NP_001254978 (NCBI)). In addition, a tBLASTx of Pp-FAR-1 against different transcriptome sets of *P. penetrans* (Vieira et al., supra), revealed two additional putative FAR members for this species, showing 36% and 31% (E-values 7.37e$^{-35}$ and 9.52e$^{-26}$, respectively) similarity to Pp-FAR-1, suggesting the presence of other FAR isoforms for *P. penetrans.*

Phylogenetic analyses revealed the relationship of Pp-FAR-1 among other nematode FARs proteins, representative species per genus of different clades among the phylum Nematoda were selected for comparison. The Pp-FAR-1 clustered together with FAR-1 of other plant-parasitic nematodes, closest to Pratylenchidae species (*P. vulnus* and *R. similis*), and separated from other clusters holding FAR proteins of animal-parasitic and free-living nematode species. The position of the two other predicted *P. penetrans* FAR proteins re-enforces the idea of the presence of different isoforms for this species.

Example 2

Pp-FAR-1 Expression Pattern Analysis

Nematodes:

A single isolate of *P. penetrans* (NL 10p RH) initially collected in Beltsville (Maryland, US), and provided by the Nematology Laboratory (USDA-ARS, USA) was maintained and multiplied in vitro in roots of corn (*Zea mays* cv. 'Iochief') growing in Murashige and Skoog (MS) medium agar plates. Nematodes were re-cultured every 2 months into new roots of corn and maintained in the dark at 28° C. For nematode extraction, infected roots were chopped into small pieces and both roots and media were placed into sterile glass bowls filled with sterile water containing 50 mg/l carbenicillin and 50 mg/l kanamycin. Nematodes were extracted 5 days later by sieving the water with a 500 μm mesh sieve, washed with sterilized distilled water and collected in a 50 mL falcon. Nematodes were then used for the experiments described herein.

Nematode Developmental Stage Expression:

RNA was extracted from approximately 150 nematodes of each nematode developmental stage. RNA was then treated with RNAase-Free DNase (Qiagen, Valencia, Calif., USA) before reverse transcription. RNA was added to the RT reaction using the iScript first-strand synthesis kit (Bio-Rad, Hercules, Calif., USA) to produce cDNA, which was posteriorly used for semi-quantitative RT-PCR and RT-qPCR analyses. Specific primers were design to amplify a Pp-far-1 fragment of 133 bp, and a 148 bp fragment of the *P. penetrans* 18S gene that was used as a reference gene. Real-time qPCR reactions included 3.5 μL of SYBR green mix (Roche), 1 μL of 5 μM primers and 100 ng of cDNA. Reactions were performed on a CFX96 Real-time system machine (BioRad). The amplification reactions were run using the following program: a hot start of 95° C. for 3 min, followed by 40 cycles of 95° C. for 10 s and 60° C. for 30 s. After 40 cycles a melt curve analysis or dissociation program (95° C. for 15 s, 60° C. for 15 s, followed by a slow ramp from 60° C. to 95° C.) was performed to ensure the specificity (above 90%) of amplification. The relative expression was quantified by the efficiency-corrected $\Delta\Delta C_T$ method, using three independent biological replicates, comprising three technical replicates.

In Situ Hybridization:

To assess localization of Pp-far-1 transcripts, whole mount in situ hybridizations were performed in all stages of *P. penetrans* following the protocol of de Boer et al. (de Boer et al., J. Nematol. (1998) 30:309-12). Specific primers were designed to amplify a 232 bp product from cDNA collected from a nematode population of mixed stages. The resulting PCR product was used as template for generation of sense and antisense DIG-labeled Pp-far-1 probes, using a DIG-nucleotide labeling kit (Roche, Indianapolis, Ind., USA). Hybridized probes within the nematode tissues were detected using anti-DIG antibody conjugated to alkaline phosphatase and its substrate. Nematode sections were then observed using a Nikon Eclipse Si light microscope.

Differential Expression in Different Host Plants:

To quantify the expression levels of Pp-far-1 during nematode-plant interaction, infected roots of corn, lily, and soybean hairy roots were used, and total RNA extraction was performed using a pool of six infected roots at 1, 3 and 7 days after nematode infection (DAI). Nematode infections of soybean hairy roots and lily plants a protocol previously described (Vieira et al., Transgenic Res. (2013) 24:421-32). In the case of corn, corn seeds were initially sterilized using 70% of ethanol for 10 min, followed by one wash in a bleach solution (20% bleach and 4 drops of Tween 20) for 15 min, four consecutive washes in sterile water, and dried under the hood for at least 30 min. Seeds were then placed in Petri dishes containing MS medium, and kept in a growth chamber with a 16 h light and 8 h dark photoperiod at 25° C., respectively. Five days later, each germinating plant was transferred to individual Petri dishes containing MS medium. Ten-day-old seedling roots were individually inoculated with approximately 400 sterilized nematodes (mixed population containing juveniles, females and males). Infected roots were collected at 1, 3 and 7 DAI, immediately frozen in liquid nitrogen, and stored at −80° C. until used. Three independent biological replicates were performed per time point and host plant. RNA and cDNA preparation, and RT-qPCR analyses were performed as described.

Figures 1B, 1C, 1D, 1E:
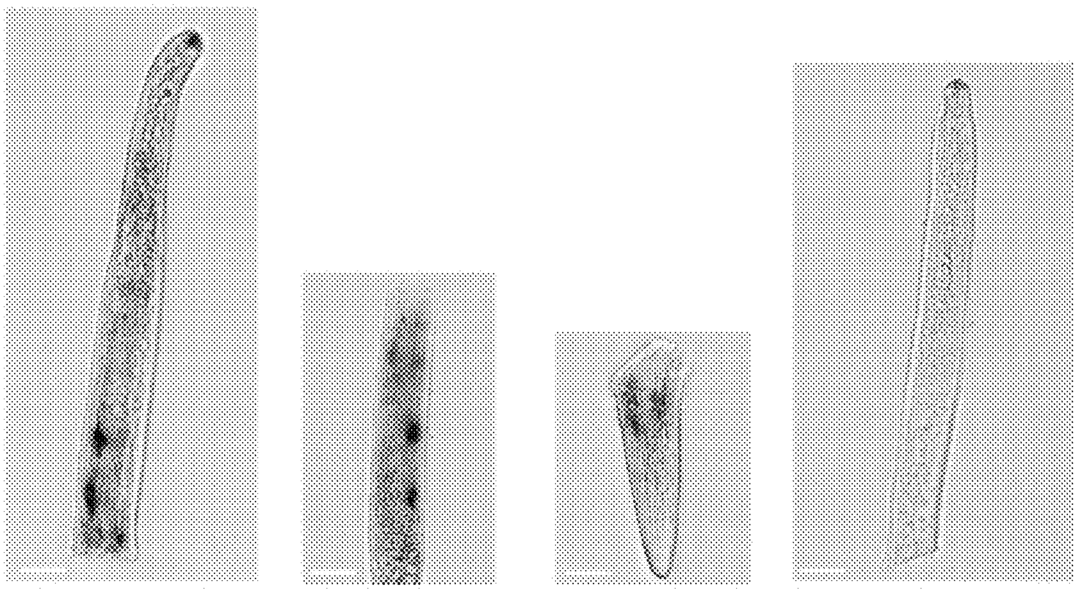

Results:

The expression of Pp-far-1 was quantified for differential nematode developmental stages [eggs, juveniles (J244), males and females] using RT-qPCR (FIG. 1). A successful amplification of Pp-far-1 was verified for all developmental stages, as well as for the 18S rRNA gene that was used as a reference gene. The lowest level of Pp-far-1 transcripts was found in eggs, which was set as unity to calculate the relative fold changes in other stages. A marked increase of Pp-far-1 transcripts could be observed for the remaining stages, with highest transcript accumulation found in juveniles, females and males, respectively (FIG. 1A). Tissue localization of the Pp-far-1 transcripts was evaluated using whole mount in situ hybridization. A positive signal was detected along different areas of the nematode body consistent with the localization of the nematode hypodermis (FIG. 1B-D). In the case of the control no signal could be detected using the sense probe (FIG. 1E).

Figure 2A:
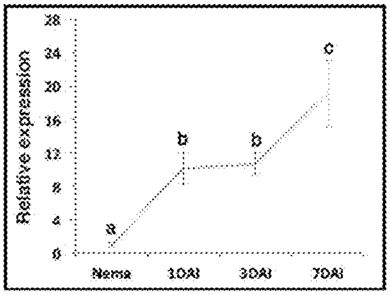
FIG. 2A-2C provide graphs showing expression levels of pp-far-1 quantified by RT-qPCR at early time points during infection within different host plants. Plants were (FIG. 2A) corn (*Zea mays* L.), (FIG. 2B) lily (*Lilium longiflorum* L.) and (FIG. 2C) soybean (*Glycines* max (L.) Merr.) hairy roots. The transcript expression levels were normalized with a *P. penetrans* 18S rRNA gene. The relative expression values represent changes of Pp-far-1 of nematodes within roots in relation to the expression levels of Pp-far-1 quantified for nematodes prior to infection. Data shown represent the means of three independent repetitions plus standard error. Letters indicate statistical significant differences between mean values among the different conditions studied ($P<0.05$).
Figure 2B:
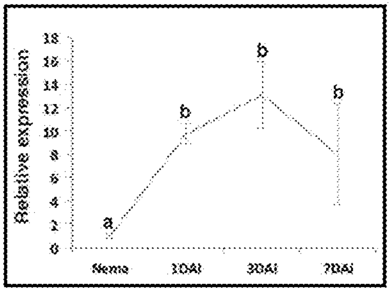
Figure 2C:
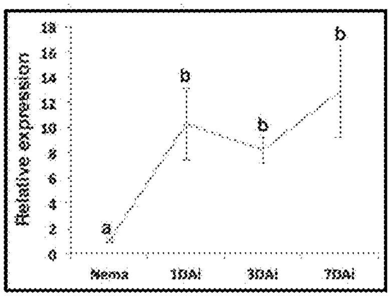

To evaluate whether the expression of the Pp-far-1 gene was host related or consistently expressed in different nematode-host interactions, we studied the expression levels of Pp-far-1 at early time points of nematode infection on corn, lily and soybean hairy roots. In this case, RNA of roots infected with *P. penetrans* was collected at 1, 3 and 7 days after infection (DAI) for each host. The expression profile of Pp-far-1 in the different hosts is presented in FIG. 2. In general an up-regulation of the Pp-far-1 gene could be observed as nematodes penetrate (1 DAI), and became established within the host (3 and 7 DAI). An 8 to 10 fold increase was registered for Pp-far-1 expression in the host-nematode interaction and at all time points tested (FIG. 2), highlighting the continuous expression of this gene during parasitism.

The expression of Pp-far-1 could be detected among all developmental stages, showing higher levels of expression for motile nematode stages. In both cyst and root-knot nematode the far-1 gene is expressed among all nematode stages but is particularly highly expressed in infective juveniles (Prior et al., supra; Iberkleid et al., supra), which corresponds to the migratory stage of these species. Different stage specific expression patterns than the one detected for Pp-far-1 were observed for the far-1 gene of other animal—(Kuang et al., Mol. Biochem. Parasitol., (2009) 168:84-94; Dillman et al., supra) or plant-parasitic species (Cheng et al., supra; Le et al., Experimental Parasitol., (2016) 167:94-102). The relative abundance of far-1 homologues varies between different species and individual nematodes stages, perhaps reflecting the array of life cycle or parasitism strategies.

Example 3

Plant-mediated RNAi Silencing of Pp-FAR-1

Generation of Transgenic Hairy Roots:

The template for the production of a Pp-far-1 dsRNA construct was amplified using nematode cDNA of mixed nematode stages. A fragment of the CDS sequence of Pp-far-1 (291 bp) was amplified with specific primers containing the CACC adapter through PCR. The nematode gene fragment was cloned into the pENTR vector (Invitrogen), following the same steps as described above for DNA sequencing. The Pp-far-1 fragment was then transferred to the pRAP17 vector (Ibrahim et al., Experimental Parasitol., (2011) 127:90-99), which is designed to express dsRNA of the target sequence. The cloning reaction was mediated using the Gateway® LR Clonase™ Enzyme Mix (Invitrogen, Carlsbad, Calif., USA). Transformation of Pp-far-1 fragment into the pRAP17 vector was confirmed by PCR using two primer pairs. The first primer pair was used to confirm the presence of the RNAi gene in the forward direction using the gene specific forward primer and intron reverse primer, while a second pair was used to confirm the presence of the Figwort Mosaic Virus promoter sub-genomic transcript and the RNAi gene in the reverse direction, using a forward primer for the FMV region and as reverse primer a gene specific region (Ibrahim et al., supra). The pRAP17 construct was then transferred to competent *Agrobacterium rhizogenes* (K559) and transformations were confirmed by PCR using the same set of primers described above, and a pair of primers to amplify a fragment of 812 bp of the *Agrobacterium* Ri plasmid (Ibrahim et al., supra). Soybean hairy root lines were then generated using the Pp-far-1 dsRNA construct, while control hairy root lines were generated using *A. rhizogenes* harboring an empty vector (pBIN-JIT) with kanamycin resistance to both bacteria and plants (Ferrandiz et al., Science, (2000) 289:436-8). Generation of soybean hairy roots was carried out according to previously reported methods (Cho et al., Planta, (2000) 10:195-204).

For confirmation of the nematode gene fragment in the transformed hairy roots, genomic DNA was isolated for PCR amplification using the FastDNA kit (MP Biomedicals). Afterwards, total RNA was isolated from 100 mg of fresh soybean hairy roots using the RNEASY PLANT MINI KIT (Qiagen, Valencia, Calif., USA) following the manufacturer's instructions. The RNA was treated with RNase-Free DNase (Qiagen, Valencia, Calif., USA) before reverse transcription. One microgram of treated RNA was added to the RT reaction using the iScript Select cDNA synthesis kit (Bio-Rad, Hercules, Calif., USA) as described by the manufacturer. The oligonucleotide primer specific for the intron of the pRAP17 vector was used to synthesize the first cDNA strand for each transformed soybean hairy root line, and the corresponding cDNAs were used as a template for amplification of a 241 bp fragment. After confirming the presence of the transgene by PCR and expression levels of the intron that separates each fragment by semi-quantitative RT-PCR, four Pp-far-1 dsRNA independent RNAi lines were selected for nematode resistance assays.

Nematode RNAi Gene Silencing Assays:

For nematode resistance tests, soybean hairy roots 3-5 cm in length were excised from stock cultures and transferred to fresh MS plates without antibiotics. Four independent lines were challenged with RLN using nine hairy root systems per line. Three control lines (containing the pBIN-JIT empty vector) were selected using nine hairy roots per line. Two weeks later, each hairy root system was inoculated with a mixed population of approximately 300 sterile *P. penetrans* and maintained in the dark at 28° C. Approximately three months after nematode inoculation, infected soybean hairy roots were chopped into small pieces and both roots and media were placed into sterile glass bowls filled with sterile water containing 50 mg/l carbenicillin and 50 mg/l kanamycin. Nematodes were extracted 5 days later by sieving the water with a 500 µm mesh sieve. Two independent nematode challenge assays were performed using the same lines. Data are expressed as the total mean number of nematodes±Standard Error of the Mean (SEM) collected for each line per challenge nematode assay. All data were analyzed using analysis of variance (ANOVA), and means were compared using Tukey's honestly significant difference (HSD) test at the 5% probability level.

For each nematode resistance test, a set of the extracted nematodes growing in each corresponding soybean hairy root line were frozen immediately in liquid nitrogen and stored at −80° C. Total RNA was isolated and reverse transcribed to cDNA as described above. Transcript abundance of Pp-far-1 was analyzed by RT-qPCR for each nematode assay, with three technical replicates. Real-time PCR reactions and analyses were carried out as described herein.

Figure 3A:
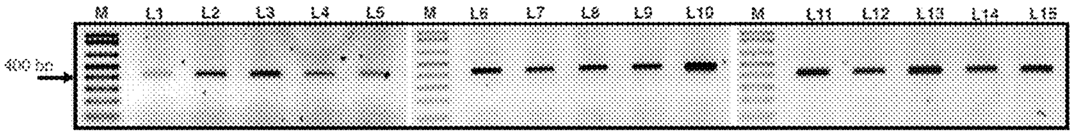
FIG. 3A-3B provide photographs of PCR analysis of soybean (*Glycines* max (L.) Merr.) hairy root lines expressing a Pp-far-1 dsRNA construct.
Figure 3B:
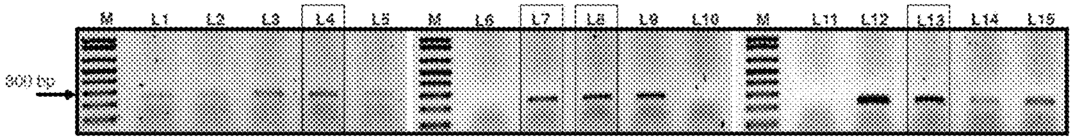
Figure 5A:
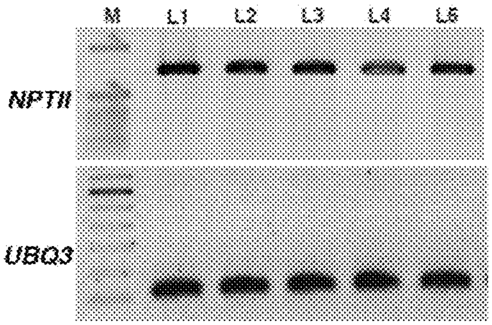
FIG. 5A-5B provide results of validation analysis of control hair root lines expressing an empty vector (pBInJIT).
Figure 5B:
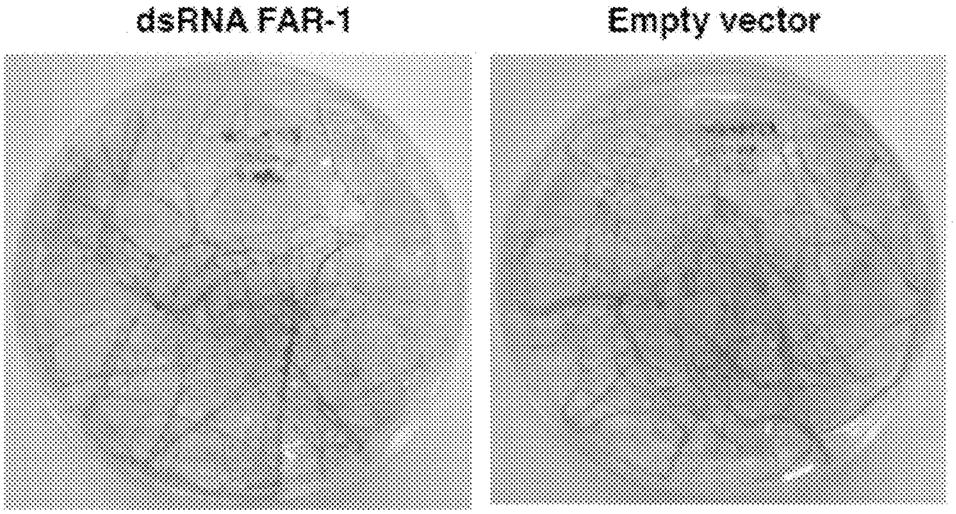

Results:

Soybean hairy roots-mediated RNAi was used to silence the expression of Pp-far-1 gene using the pRAP17 vector (Ibrahim et al., supra), using a 291 bp fragment located at the C-terminal region. A total of 15 independent transgenic dsRNA hairy root lines were initially generated and used for molecular characterization (FIG. 3A). The presence of the Pp-far-1 fragment was validated by PCR, using a forward primer located in the FMV promoter region and a reverse primer located in the nematode fragment, resulting in a fragment of 420 bp (FIG. 3B). The expression levels of the dsRNA constructs were evaluated by semi-quantitative RT-PCR using the amplification of a fragment of 241 bp of the pRAP17 intron (FIG. 3B). For nematode challenge assays four lines (L4, L7, L8 and L13) were chosen based on the intron expression and growth performance (hairy root lines growing weakly were not selected for nematode challenge assays). Lines transformed with pBinJIT empty vector (L1, L3 and L4) were used as control (FIG. 5A-5B). In comparison to control lines, no apparent phenotypic variation could be observed between the selected lines for nematode challenge assays (data not shown).

Figure 4A:
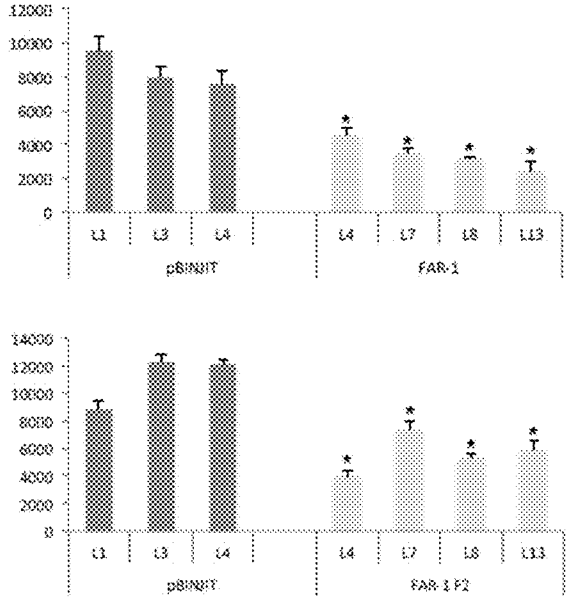
FIG. 4A-4B provide graphs showing the effects RNAi on *P. penetrans*.
Figure 4B:
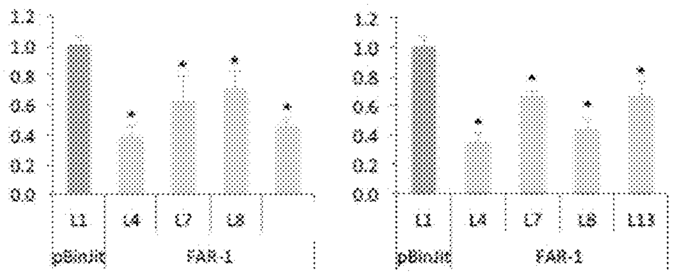

To evaluate whether the in planta expression of Pp-far-1 dsRNA fragment had any effect on nematode development/reproduction, the total number of nematodes associated with each soybean hairy root lines was quantified three months after nematode inoculation. Two independent nematode challenge assays were performed using the same lines, and data is presented as the total average number of nematodes recovered for each individual line (FIG. 4A-4B). A significant reduction ($P<0.05$) of the total number of nematodes developing in hairy roots expressing Pp-far-1 dsRNA in both nematode challenge assays was observed, ranging from a total of 44% to 70% less nematodes in comparison to the average number of nematodes counted for the control lines (FIG. 4A).

To confirm the silencing effect on the nematode Pp-far-1 transcript levels, total RNA was extracted from a mixture of nematode stages (eggs, juveniles and adults) developing on individually transformed hairy roots lines as compared to control lines. Our results showed that the silencing effect among the different lines showed some variability, although when comparing with control, a significant reduction ($P<0.05$) of the Pp-far-1 transcripts could be observed, suggesting an effective knockdown of Pp-far-1 nematode gene (FIG. 4B).

Once interacting with the plant, the expression profiles of Pp-far-1 showed a significant transcript up-regulation in all the hosts tested, highlighting the importance of far-1 during interaction of *P. penetrans* with the plant. As presented herein, host-mediated silencing by production of a far-1 dsRNA fragment in hairy roots of soybean was used to knockdown the far-1 gene of *P. penetrans*. Our RNAi assays validated the importance of Pp-FAR-1 during this plant-host interaction, as silencing of Pp-far-1 resulted up to a 70% reduction of the total number nematodes in comparison to control roots. Our results demonstrated that silencing the Pp-far-1 gene in *P. penetrans* had a substantial detrimental effect on the nematode development. Thus inhibition of Pp-far-1 expression through RNAi could be seen as an effective approach to target and control root lesion nematodes.

Example 4

Uptake of Pp-FAR-1 dsRNA by Target Plants dsRNA with one strand identical to SEQ ID NO:1, 2 or 3 is prepared in vitro by any method available in the art. 10 mL solution of the dsRNA in ddH20 containing approximately 400 ng/mL is applied to the test plant (soybean, lily or corn) via root soaking, or foliar spray. The dsRNA is taken up by the treated plant and plant tissues (roots, leaves) are analyzed for the presence of dsRNA by PCR. Presence of the dsRNA in the plant tissues of interest indicate the dsRNA can be ingested by a feeding nematode to induce RNAi in a similar manner to that described in Example 3 above.

While the invention has been described with reference to details of the illustrated embodiments, these details are not intended to limit the scope of the invention as defined in the appended claims. The embodiment of the invention in which exclusive property or privilege is claimed is defined as follows:

What is claimed is:

1. A double-stranded ribonucleic acid (dsRNA) comprising a first strand comprising a sequence with at least 95% identity to a portion of at least 19 consecutive nucleotides of SEQ ID NO:1 or SEQ ID NO:3 and a second strand complementary to the first strand.

2. The dsRNA of claim 1, wherein the first strand has at least 99% sequence identity to any one of SEQ ID NO:1, or SEQ ID NO:3.

3. The dsRNA of claim 1 or claim 2, wherein the first strand comprises SEQ ID NO: 1.

4. The dsRNA of claim 1 or claim 2, wherein the first strand comprises SEQ ID NO: 3.

5. A double-stranded ribonucleic acid (dsRNA) comprising a first strand comprising a sequence with at least 95% identity to a portion of at least 24 consecutive nucleotides of SEQ ID NO:1, SEQ ID NO:2, or SEQ ID NO:3 and a second strand complementary to the first strand.

6. The dsRNA of claim 5, wherein the first strand has at least 99% identity to SEQ ID NO: 2.

7. The dsRNA of claim 1 or claim 2 or claim 5, wherein the dsRNA is expressed in a plant cell.

8. The dsRNA of claim 1 or claim 2 or claim 5, wherein the dsRNA is distributed throughout at least part of a living plant.

9. The dsRNA of claim 8, wherein the plant is corn, soybean or lily.

10. The dsRNA of claim 1 or claim 2 or claim 5, wherein the dsRNA capable of inducing ribonucleic acid interference (RNAi) when ingested by a nematode.

11. The dsRNA of claim 10, wherein the nematode is *Pratylenchus penetrans*.

12. A DNA molecule comprising a promoter functional in a host cell and a DNA encoding a dsRNA comprising a first strand and a second strand, wherein the first strand comprises a sense region with at least 95% sequence identity a portion of at least 24 consecutive nucleotides of SEQ ID NO:1, SEQ ID NO:2, or SEQ ID NO:3 and a second strand complementary to the first strand.

13. The DNA molecule of claim 12, wherein the host cell is a plant cell.

14. A host cell comprising the DNA molecule of claim 12.

15. A plant cell, plant or seed comprising a dsRNA of claim 1 or claim 2.

16. The plant cell, plant or seed of claim 15, wherein the plant cell, plant or seed comprises the DNA molecule of claim 12.

17. A method of inducing RNAi in a nematode, comprising allowing the nematode to feed on a plant comprising the dsRNA of claim 1 or claim 2 or claim 5 such that the dsRNA is ingested by the nematode, thereby inducing RNAi.

18. The method of claim 17, wherein the dsRNA wherein the first strand of the dsRNA comprises SEQ ID NO: 1.

19. The method of claim 17, wherein the dsRNA wherein the first strand of the dsRNA comprises SEQ ID NO: 2.

20. The method of claim 17, wherein the dsRNA wherein the first strand of the dsRNA comprises SEQ ID NO: 3.

21. The method of claim 17, wherein the plant is corn, lily or soybean.

* * * * *